(12) United States Patent
Roxas et al.

(10) Patent No.: US 10,695,549 B2
(45) Date of Patent: Jun. 30, 2020

(54) ADAPTER FOR MEDICAL CONNECTORS

(71) Applicant: Fenwal, Inc., Lake Zurich, IL (US)

(72) Inventors: James Darren Roxas, Chicago, IL (US); Chaitra Kishore, Palatine, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/644,077

(22) Filed: Jul. 7, 2017

(65) Prior Publication Data

US 2018/0008812 A1    Jan. 11, 2018

Related U.S. Application Data

(60) Provisional application No. 62/360,148, filed on Jul. 8, 2016.

(51) Int. Cl.
| | | |
|---|---|---|
| *A61M 39/10* | (2006.01) | |
| *A61M 1/36* | (2006.01) | |
| *A61M 39/20* | (2006.01) | |

(52) U.S. Cl.
CPC ............ *A61M 39/10* (2013.01); *A61M 1/367* (2013.01); *A61M 39/20* (2013.01);
(Continued)

(58) Field of Classification Search
CPC ...... A61M 39/10; A61M 1/367; A61M 39/20; A61M 2039/1077; A61M 2039/1083; A61M 2039/1088; A61M 2039/1094
See application file for complete search history.

(56) References Cited

U.S. PATENT DOCUMENTS

| | | | | |
|---|---|---|---|---|
| 4,294,250 A | * | 10/1981 | Dennehey | ............. A61M 39/10 604/403 |
| 5,052,725 A | * | 10/1991 | Meyer | ................. F16L 37/0841 285/308 |

(Continued)

FOREIGN PATENT DOCUMENTS

| | | |
|---|---|---|
| EP | 3042691 A1 | 7/2016 |
| WO | WO 2015/034045 A1 | 3/2015 |

OTHER PUBLICATIONS

Partial European Search Report for EP Application No. 17180162.4 dated Nov. 16, 2017.

(Continued)

*Primary Examiner* — Nathan R Price
*Assistant Examiner* — Anh Bui
(74) *Attorney, Agent, or Firm* — Cook Alex Ltd.

(57) ABSTRACT

An adapter for making a fluid connection between first and second medical fluid flow components, where the first component includes a first male or female Luer connector of a first configuration, and the component includes a second male female Luer connector of a second configuration, that is not compatible with the first configuration, includes a fluid flow conduit with a first adapter connector at a first end of the conduit and a second adapter connector at a second end of the conduit. The conduit includes a fluid flow lumen extending between the first and second ends. The first adapter connector is a male or female Luer having a first configuration that is compatible with the first medical fluid flow component connector. The second adapter connector is a male or female Luer having a second configuration that is compatible with the second medical fluid flow component connector.

17 Claims, 15 Drawing Sheets

(52) U.S. Cl.
CPC ............... *A61M 2039/1033* (2013.01); *A61M 2039/1077* (2013.01); *A61M 2039/1083* (2013.01); *A61M 2039/1088* (2013.01); *A61M 2039/1094* (2013.01); *A61M 2205/586* (2013.01)

(56) References Cited

U.S. PATENT DOCUMENTS

| | | | | |
|---|---|---|---|---|
| 5,139,483 | A * | 8/1992 | Ryan | A61M 39/1011 604/533 |
| 5,312,377 | A * | 5/1994 | Dalton | A61M 39/10 285/331 |
| 5,620,427 | A * | 4/1997 | Werschmidt | A61M 39/10 137/516.13 |
| 5,651,776 | A | 7/1997 | Appling et al. | |
| 5,685,858 | A * | 11/1997 | Kawand | A61M 39/0606 604/167.01 |
| 5,702,374 | A * | 12/1997 | Johnson | A61M 39/10 128/912 |
| 5,782,505 | A * | 7/1998 | Brooks | A61M 39/12 285/148.19 |
| 6,309,543 | B1 * | 10/2001 | Fenton | B01D 61/30 210/232 |
| 6,997,919 | B2 * | 2/2006 | Olsen | A61M 39/12 604/535 |
| 8,372,057 | B2 * | 2/2013 | Cude | A61M 39/10 604/240 |
| 9,289,587 | B2 * | 3/2016 | Colman | A61M 39/1011 |
| 2006/0047251 | A1 * | 3/2006 | Bickford Smith | A61M 39/10 604/240 |
| 2006/0293640 | A1 * | 12/2006 | Greco | A61J 1/2096 604/411 |
| 2007/0060898 | A1 * | 3/2007 | Shaughnessy | A61M 39/10 604/284 |
| 2007/0088325 | A1 * | 4/2007 | Fangrow, Jr. | A61M 39/10 604/533 |
| 2007/0129705 | A1 * | 6/2007 | Trombley, III | A61M 39/10 604/523 |
| 2008/0140055 | A1 * | 6/2008 | Shirley | A61J 15/0015 604/535 |
| 2010/0063482 | A1 * | 3/2010 | Mansour | A61M 39/26 604/539 |
| 2011/0079095 | A1 * | 4/2011 | Bruecher | C12M 33/04 73/864.63 |
| 2011/0130717 | A1 * | 6/2011 | David | A61M 5/3134 604/68 |
| 2011/0282303 | A1 * | 11/2011 | Hornig | A61M 39/223 604/248 |
| 2012/0123392 | A1 | 5/2012 | McKinnon et al. | |
| 2012/0197205 | A1 * | 8/2012 | Peters | A61M 25/02 604/180 |
| 2013/0270819 | A1 * | 10/2013 | Amborn | A61M 39/10 285/328 |
| 2015/0265828 | A1 | 9/2015 | Colman | |
| 2016/0001056 | A1 * | 1/2016 | Nelson | A61M 39/045 604/247 |
| 2016/0325086 | A1 * | 11/2016 | Lauer | A61M 39/1011 |
| 2016/0339226 | A1 * | 11/2016 | Sealfon | A61M 39/20 |
| 2016/0367439 | A1 * | 12/2016 | Davis | A61J 1/2096 |

OTHER PUBLICATIONS

International Organization for Standardization, International Standard ISO 594-1 Conical Fittings with a 6% (Luer) Taper for Syringes, Needles and Certain Other Medical Equip.
International Organization for Standardization, International Standard ISO 594-2 Conical Fittings with 6% (Luer) Taper for Syringes, Needles and Certain Other Medical Equipme.
Connectors for reservoir delivery systems for healthcare applications—Part 7: Connectors for intravascular infusion, Association for the Advancement of Medical Instrumentation.

* cited by examiner

ADAPTER FOR MEDICAL CONNECTORS

CLAIM OF PRIORITY

This application claims the benefit of U.S. Provisional Application No. 62/360,148, filed Jul. 8, 2016, the contents of which are hereby incorporated by reference.

FIELD OF THE INVENTION

The present disclosure relates generally to connectors for medical fluid flow systems and, in particular, to an adapter for joining or sealing medical fluid flow systems or component thereof that feature connectors of differing configurations.

BACKGROUND

Medical fluid flow systems often employ fluid flow connectors, such as Luer connectors, to readily connect components in a liquid leak-proof manner. Compatible connectors typically include a male connector and a female connector. The male connector features a conical male member having a Luer taper that corresponds to the Luer taper of the socket of the female connector. Fluid flow passages within the connectors communicate with openings in the tip of the tapered male member and the inner end wall of the socket of the female connector.

The male and female Luer connectors are joined by inserting the male conical member into the female socket and pushing the two connectors together. The two connectors are secured together by the friction of their mating tapered surfaces. Although such a connection may be suitable for many medical purposes, it is common to employ additional retaining or locking features to hold the male and female Luer connectors together and reduce the risk of accidental disconnection. For example, an internally threaded collar may be provided on one of the connectors and mating threads on the exterior surface of the other connector. Such connectors are commonly referred to as Luer lock connectors.

Industry standards have been established for standardizing the dimensions of Luer connectors and Luer lock connectors for use in medical equipment. An example of such a standard is the International Organization for Standardization International Standard ISO 594.

An example of an ISO 594 male connector is indicated in general at 30 in FIGS. 1 and 2, and includes a conical member 32 with a Luer taper. An annular collar 34 is provided with threads 36 on the inward facing surface. A shaft portion 38 includes a fluid flow passage 42 that is in fluid communication with a flow passage 44 formed in conical member 32. The shaft portion 38 is adapted to be connected to tubing or other medical fluid flow components.

An example of an ISO 594 female connector is indicated in general at 50 in FIGS. 3 and 4, and includes a cylindrical portion 52 having a socket 54 that features a Luer taper and receives the conical member 32 of FIGS. 1 and 2. The exterior surface of the cylindrical portion is provided with threads 56 that are compatible with the threads 36 of FIGS. 1 and 2. A body portion 58 includes a fluid flow passage 62 that is in fluid communication with socket 54 through the inner end thereof. The body portion 58 is adapted to be connected to tubing or other medical fluid flow components. Also either the male or female connector may be actually integral with a medical flow component. For example, a syringe may have a one-piece molded plastic barrel that terminates with a male Luer lock connector.

FIG. 5 illustrates the ISO 594 male Luer connector 30 of FIGS. 1 and 2 joined to the ISO 594 female Luer connector 50 of FIGS. 3 and 4. The tapered conical member 32 of the male connector is received within, and engages the inner surface of, the tapered socket 54 of the female connector, while the threads 56 of the female connector engage the threads 36 of the collar 34 of the male connector.

A new international standard for Luer connectors has recently been introduced or proposed, and is particularly directed to connectors used in apheresis procedures, where blood is withdrawn from a donor, a portion (such as plasma, leukocytes, or platelets) is separated and retained, and the remainder is re-transfused into the donor. The new standard, International Standard ISO 18250, relates to a male apheresis Luer connector and a female apheresis Luer connector for use in apheresis disposable sets and other apheresis components.

An example of an ISO 18250 male Luer connector is indicated in general at 70 in FIGS. 6 and 7, and includes a conical member 72 with a tapered portion and a larger diameter annular offset or shoulder portion 73. An annular collar 74 is provided with threads 76 on the exterior surface. A shaft portion 78 includes a fluid flow passage 82 that is in fluid communication with a flow passage 84 formed in conical member 72. The shaft portion 78 is adapted to be connected to tubing or other medical fluid flow components.

An example of an ISO 18250 female Luer connector is indicated in general at 90 in FIGS. 8 and 9, and includes a cylindrical portion 92 having a socket that features a tapered portion 93 and a taper offset entry portion 95 having an enlarged diameter than tapered portion 93. Socket tapered portion 93 receives the conical member 72 of FIGS. 6 and 7 while the socket offset portion 95 receives the annular shoulder portion 73 of FIG. 7. An annular collar 94 is provided with threads 96 on the inward facing surface that are compatible with the threads 76 of FIGS. 6 and 7. A shaft portion 98 is adapted to be connected to tubing or other medical fluid flow components.

FIG. 10 illustrates the ISO 18250 male Luer connector 70 of FIGS. 6 and 7 joined to the ISO 18250 female Luer connector 90 of FIGS. 8 and 9. The tapered conical member 72 of the male connector is received within, and engages the inner surface of, the socket tapered portion 93 of the female connector, while the threads 96 of the collar 94 of the female connector engage the threads 76 of the collar 74 of the male connector. In addition, the socket offset portion 95 of the female connector receives and engages the annular shoulder portion 73 of the male connector.

The intent of ISO 18250 is that all apheresis disposable sets will eventually use ISO 18250 male and female Luer connectors. Most apheresis disposable sets, however, currently use ISO 594 Luer connectors, which are incompatible with the ISO 18250 connectors. For example, as may be seen by a comparison of FIGS. 1 and 2 with FIGS. 6 and 7, the collar of the ISO 594 male Luer connector has threads on the inner surface, while the collar of the ISO 18250 male apheresis Luer connector has threads on the exterior surface. Likewise, a comparison of FIGS. 3 and 4 with FIGS. 8 and 9 reveals that the ISO 594 female Luer connector has threads on the exterior surface while the ISO 18250 female apheresis Luer connector has threads on the inner surface of a collar. Furthermore, the annular shoulder portions 73 (FIG. 7) of the ISO 18250 male Luer connector and the corresponding socket offset portion 95 (FIG. 9) of the ISO 18250 female Luer connector are missing from the male and female ISO 594 Luer connectors. In addition, dimensional differences exist between the ISO 594 and the ISO 18250 Luer connectors.

A further issue exists in that most disposable apheresis sets are used in conjunction with separate solution bags. A proper connection between the two requires compatible connectors (i.e. a female connector and male connector of the same type or configuration). For example, if a solution bag has an ISO 594 female Luer connector, then the part of the disposable set that feeds into the connection must have an ISO 594 male Luer connector. Most solution bags used with apheresis disposable sets currently use either an ISO 594 male Luer connector or an ISO 594 female Luer connector, so a compatibility issue exists with respect to disposable apheresis sets that feature ISO 18250 Luer connectors.

The above problems are magnified in that a long time period will likely be required for manufacturers of medical components to changeover to the ISO 18250 standard. In addition, some companies may choose not to follow the new ISO 18250 standard at all. This may result in a supply chain problem or disruption. As an example, a medical center may order solution bags from a first company that has changed over to the ISO 18250 standard. The medical center may also order apheresis disposable sets from a second company that still uses ISO 594 Luer connectors. In such a situation, the disposable set will not be able to connect to the solution bag during an apheresis procedure. This may require the medical center to stock duplicative items having different connector configurations, increasing cost, wastage and the risk of faulty connections of incompatible connectors.

SUMMARY

Figure 1:
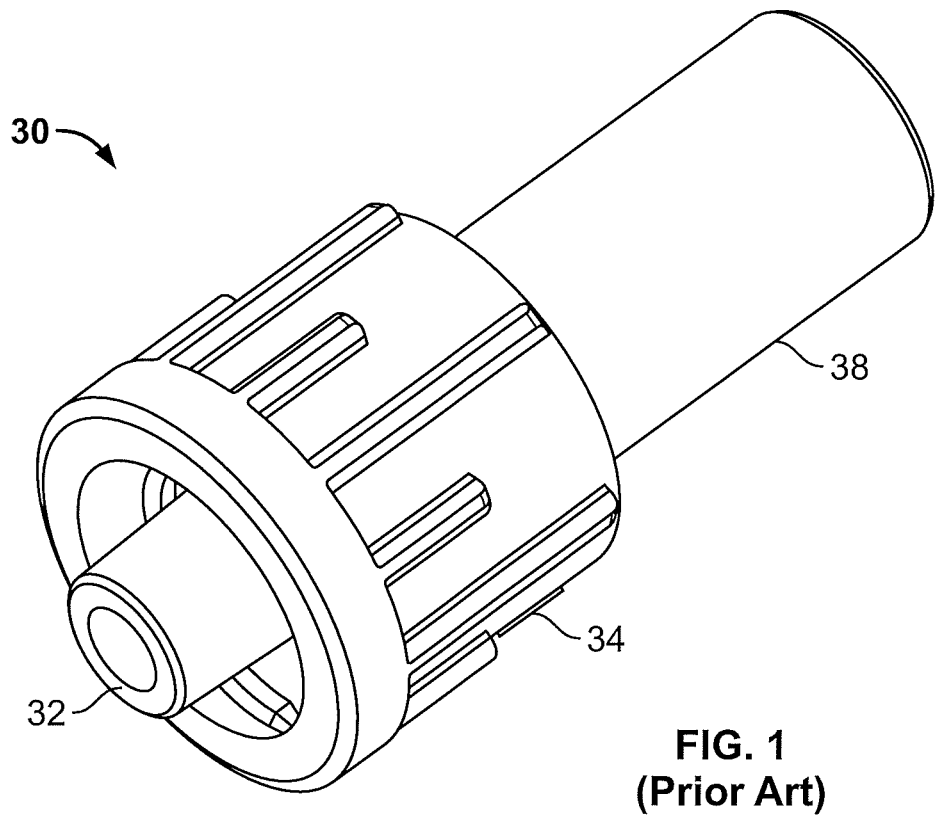
FIG. 1 is a perspective view of an ISO 594 male Luer connector.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an adapter is provided for making a fluid connection between first and second medical fluid flow components in which the first medical fluid flow component includes a first male Luer or female Luer connector of a first configuration, and the second medical fluid flow component includes a second male Luer or female Luer connector of a second configuration that is not compatible with the first configuration. The adapter includes a fluid flow conduit including a first end and a second end and a fluid flow lumen extending between the first and second ends. A first adapter connector is at the first end of the conduit. The first adapter connector is a male Luer or female Luer having a first configuration compatible with the first medical fluid flow component connector. A second adapter connector is at the second end of the conduit. The second adapter connector is a male Luer or female Luer having a second configuration compatible with the second medical fluid flow component connector.

In another aspect, a cap is provided for closing fluid flow access to a medical fluid flow component having a male or female Luer connector of a first configuration or a second configuration, or for making a closed fluid flow blocking connection between first and second medical fluid flow components in which the first medical fluid flow component includes a first male Luer or female Luer connector of a first configuration, and the second medical fluid flow component includes a second male Luer or female Luer connector of a second configuration that is not compatible with the first configuration. The cap includes a member including a first end and a second end. A first cap connector is at the first end of the member. The first cap connector is a male Luer or female Luer having a first configuration compatible with the first medical fluid flow component connector. A second cap connector is at the second end of the member. The second cap connector is a male Luer or female Luer having a second configuration compatible with the second medical fluid flow component connector.

In further aspect, an adapter is provided for making a fluid connection between first and second apheresis fluid flow components in which the first apheresis fluid flow component includes a first male Luer or female Luer connector that is compliant with an apheresis connector technical standard, and the second apheresis fluid flow component includes a second male Luer or female Luer connector that is compliant with the apheresis connector technical standard. The adapter features a fluid flow conduit including a first end and a second end and a fluid flow lumen extending between the first and second ends. A first adapter connector is at the first end of the conduit and is a male Luer or female Luer having a first configuration compatible with the first apheresis fluid flow component connector. A second adapter connector is at the second end of the conduit and is a male Luer or female Luer having a second configuration compatible with the second apheresis fluid flow component connector.

In a further aspect, a cap is provided for closing fluid flow access to an apheresis fluid flow component having a male or female connector of a first configuration or a second configuration, or for and making a closed fluid flow blocking connection between first and second apheresis fluid flow components in which the first apheresis fluid flow component includes a first male Luer or female Luer connector that is compliant with an apheresis connector technical standard, and the second apheresis fluid flow component includes a second male Luer or female Luer connector that is compliant with the apheresis connector technical standard. The cap features a member including a first end and a second end and a first adapter connector at the first end of the member that is a male Luer or female Luer having a first configuration compatible with the first apheresis fluid flow component connector. A second adapter connector is at the second end of the member and is a male Luer or female Luer having a second configuration compatible with the second apheresis fluid flow component connector.

In another aspect, a method is provided for making a fluid connection between first and second medical fluid flow components in which the first medical fluid flow component includes a first male Luer or female Luer connector of a first configuration, and the second medical fluid flow component includes a second male Luer or female Luer connector of a second configuration that is not compatible with the first configuration. The method includes the steps of connecting the first medical fluid flow component connector to a first adapter male or female connector having a configuration compatible with the first medical fluid flow connector and connecting the second medical fluid flow component connector to a second adapter male or female connector having a configuration compatible with the second medical fluid flow connector.

In another aspect, a method is provided for closing fluid flow access to a medical fluid flow component having a male or female Luer connector of a first configuration or a second configuration, or for making a closed fluid flow blocking connection between first and second medical fluid flow components in which the first medical fluid flow component includes a first male Luer or female Luer connector of a first configuration, and the second medical fluid flow component includes a second male Luer or female Luer connector of a second configuration that is not compatible with the first configuration. The method includes the steps of connecting the first medical fluid flow component connector to a first cap male or female connector having a configuration compatible with the first medical fluid flow connector and connecting the second medical fluid flow component connector to a second cap male or female connector having a configuration compatible with the second medical fluid flow connector.

In further aspect, a medical fluid flow system is provided that includes first and second medical fluid flow components in which the first medical fluid flow component includes a first male Luer or female Luer connector of a first configuration, and the second medical fluid flow component includes a second male Luer or female Luer connector of a second configuration that is not compatible with the first configuration. The system also includes an adapter making a fluid connection between first and second medical fluid flow components where the adapter features a fluid flow conduit including a first end and a second end and a fluid flow lumen extending between the first and second ends. A first adapter connector is at the first end of the conduit and is a male Luer or female Luer having a first configuration compatible with the first medical fluid flow component connector. A second adapter connector is at the second end of the conduit and is a male Luer or female Luer having a second configuration compatible with the second medical fluid flow component connector.

DETAILED DESCRIPTION OF EMBODIMENTS

While embodiments of the adapter of the disclosure are described with regard to International Standards ISO 594 and ISO 18250, it is to be understood that the adapter may include connectors that conform to any alternative standard or connectors that are not covered by any industry standard. In addition, while the embodiments of the disclosure are described and illustrated using an apheresis disposable set and a solution bag as non-limited examples of the medical components, other components known in the art may be joined by the adapters. Furthermore, while embodiments of the adapter of the disclosure are described as joining two medical components, embodiments joining three or more medical components may alternatively be constructed.

The term "adapter" is to be interpreted as including any device that is capable of joining two or more medical fluid flow components together, either with or without (such as in the case of a cap) the components being in fluid communication with one another as a result. Actual joining of two or more components together is not required, e.g., use as a cap for a single component.

Furthermore, when a connector is referred to in terms of a standard, it is to be interpreted as the connector being made in accordance with the referenced standard. For example, an ISO 594 male or female Luer connector is a male or female Luer connector that is made in accordance with the ISO 594 standard. As another example, an ISO 18250 male or female connector is a male or female connector that is made in accordance with the ISO 18250 standard.

Embodiments of the adapter are preferably integrally molded or otherwise formed as one-piece from a material such as a substantially rigid plastic, but other materials known in the art may be used. Alternatively, the adapter may be formed from individual parts that are separately formed and then joined.

Figure 2:
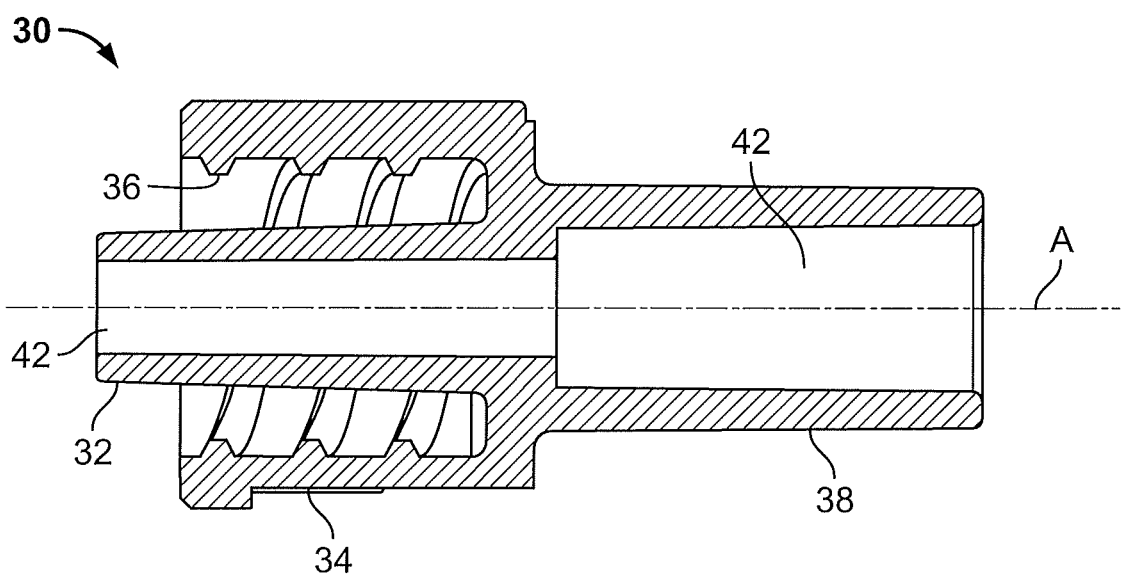
FIG. 2 is a cross sectional view of the connector of FIG. 1 with the cutting plane parallel to, and passing through, the longitudinal axis of the connector, indicated at A.
Figure 6:
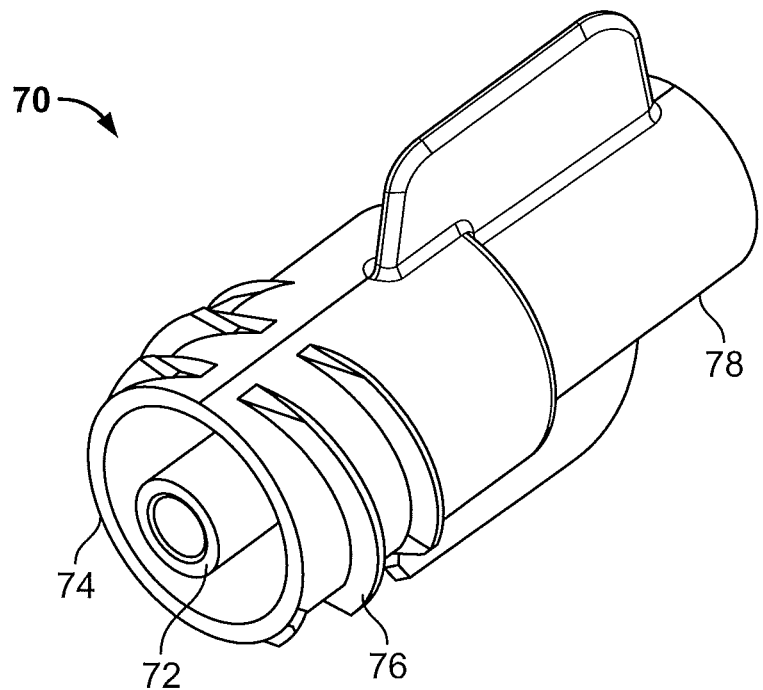
FIG. 6 is a perspective view of an ISO 18250 male Luer connector.
Figure 7:
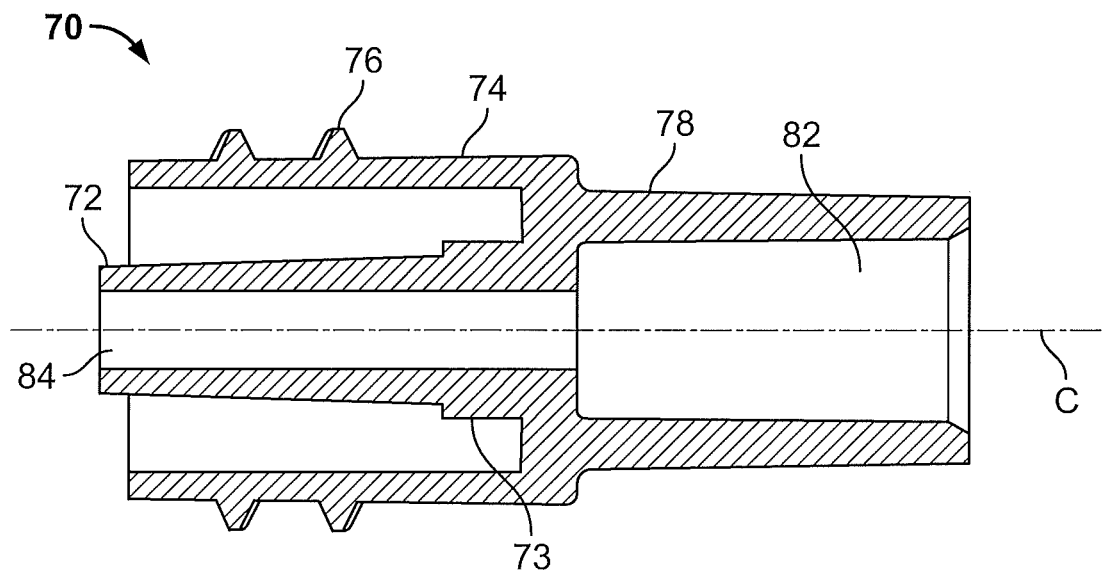
FIG. 7 is a cross sectional view of the connector of FIG. 6 with the cutting plane parallel to, and passing through, the longitudinal axis of the connector, indicated at C.
Figure 11:
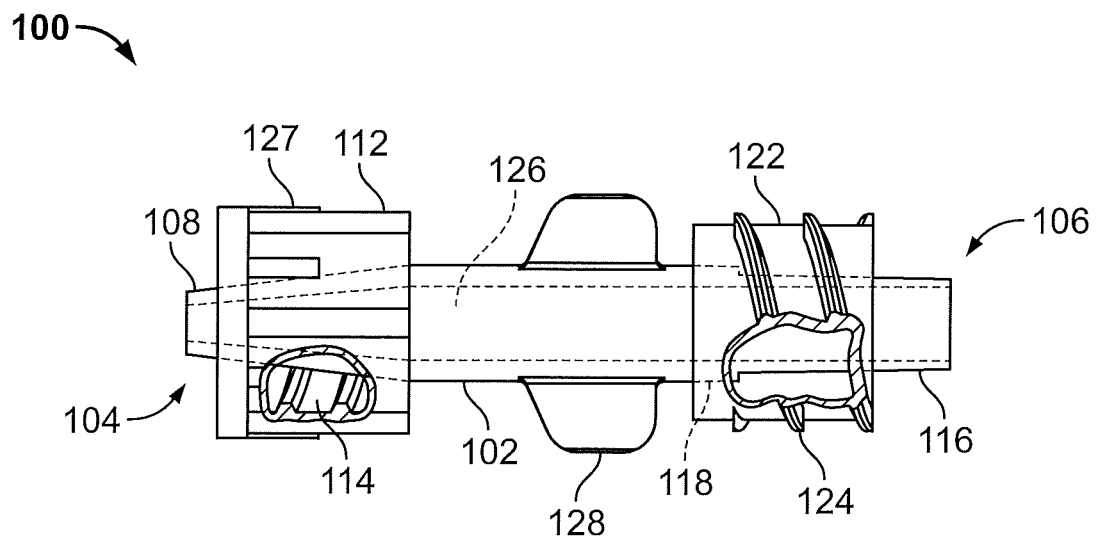
FIG. 11 is a partially broken away, side elevational view of a first embodiment of the adapter of the disclosure.

A first embodiment of the adapter of the disclosure is indicated in general at 100 in FIG. 11. The adapter includes a member or fluid flow conduit 102 having a male Luer connector in accordance with one configuration, e.g., an ISO 594 male Luer connector, indicated in general at 104, positioned on one end and a male Luer connector in accordance with a different configuration, e.g., an ISO 18250 male Luer connector, indicated in general at 106, positioned on the other end. While a rigid conduit or member is illustrated in the present and following embodiments, the conduit or member may instead be made of a flexible material, such as, as examples only, a tube or connecting member such as a flexible cord. The ISO 594 male Luer connector, as described above with reference to FIGS. 1 and 2, includes a conical member 108 with a Luer taper. An annular collar 112 is provided with threads 114 on the inward facing surface. The ISO 18250 male Luer connector 106, as described above with reference to FIGS. 6 and 7, includes a conical member with a tapered portion 116 and an annular offset or shoulder portion 118. An annular collar 122 is provided with threads 124 on the exterior surface. A central fluid flow lumen 126 extends through the fluid flow conduit 102 and the connectors 104 and 106. As a result, the adapter 100 may be used to join a medical component featuring an ISO 594 female Luer connector (which is joined to connector 104) to a separate medical component featuring an ISO 18250 female Luer connector (which is joined to connector 106) so that the two components are in fluid communication with one another.

The exterior of the collar 112 of the connector 104 of FIG. 11 may be provided with raised ribs 127 for gripping and turning the adapter while connector 104 is being joined to a compatible connector. One or more wings 128 are also preferably provided on the exterior surface of the fluid flow conduit 102 for receipt between a user's finger tips for gripping and turning while the connector 106 (or connector 104) is being joined to a compatible connector.

Figure 8:
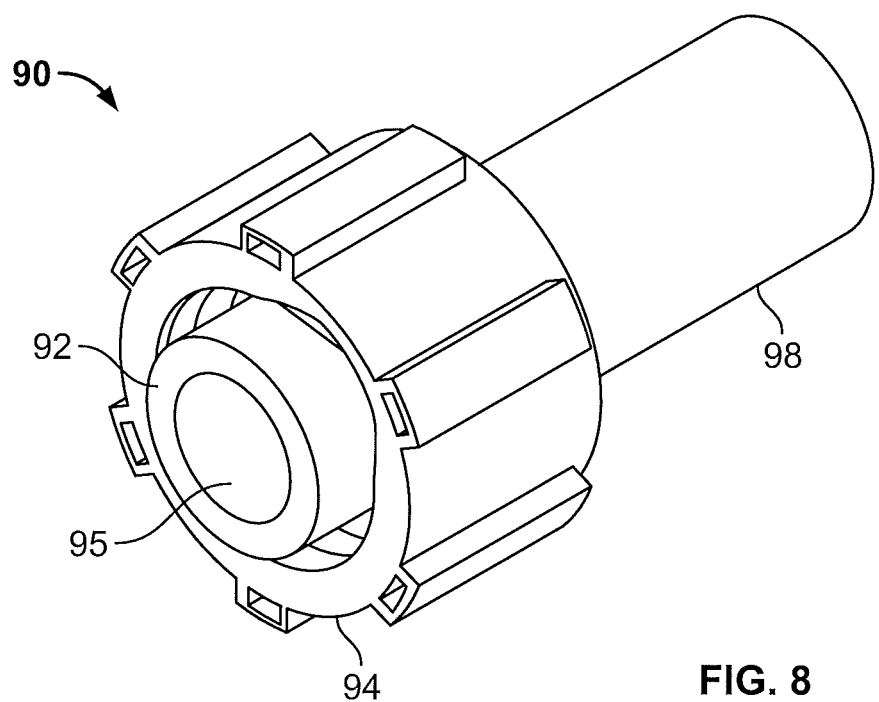
FIG. 8 is a perspective view of an ISO 18250 female Luer connector.
Figure 9:
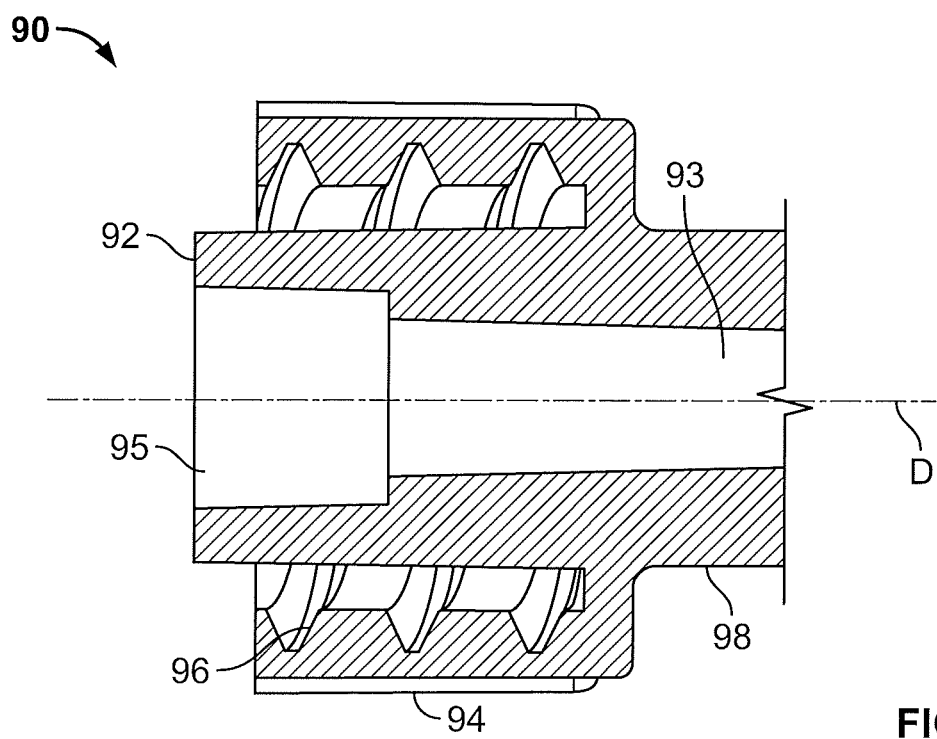
FIG. 9 is a cross sectional view of the connector of FIG. 8 with the cutting plane parallel to, and passing through, the longitudinal axis of the connector, indicated at D.
Figure 12:
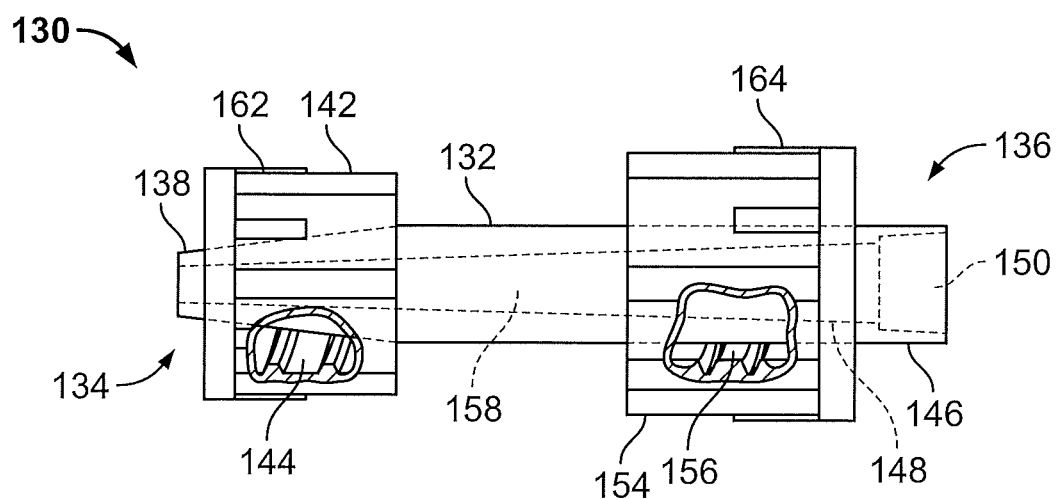
FIG. 12 is a partially broken away, side elevational view of a second embodiment of the adapter of the disclosure.

A second embodiment of the adapter of the disclosure is indicated in general at 130 in FIG. 12. The adapter includes a fluid flow conduit 132 having an ISO 594 male Luer connector, indicated in general at 134, positioned on one end and an ISO 18250 female Luer connector, indicated in general at 136, positioned on the other end. The ISO 594 male Luer connector, as described above with reference to FIGS. 1 and 2, includes a conical member 138 with a Luer taper. An annular collar 142 is provided with threads 144 on the inward facing surface. The ISO 18250 female Luer connector 136, as described above with reference to FIGS. 8 and 9, includes a cylindrical portion 146 having a socket that features a tapered portion 148 and a taper offset entry portion 150 having an enlarged diameter. An annular collar 154 is provided with threads 156 on the inward facing surface.

A central fluid flow lumen 158 extends through the fluid flow conduit 132 and the connectors 134 and 136. As a result, the adapter 130 may be used to join a medical component featuring an ISO 594 female Luer connector (which is joined to connector 134) to a separate medical component featuring an ISO 18250 male Luer connector (which is joined to connector 136) so that the two components are in fluid communication with one another.

Figure 10:
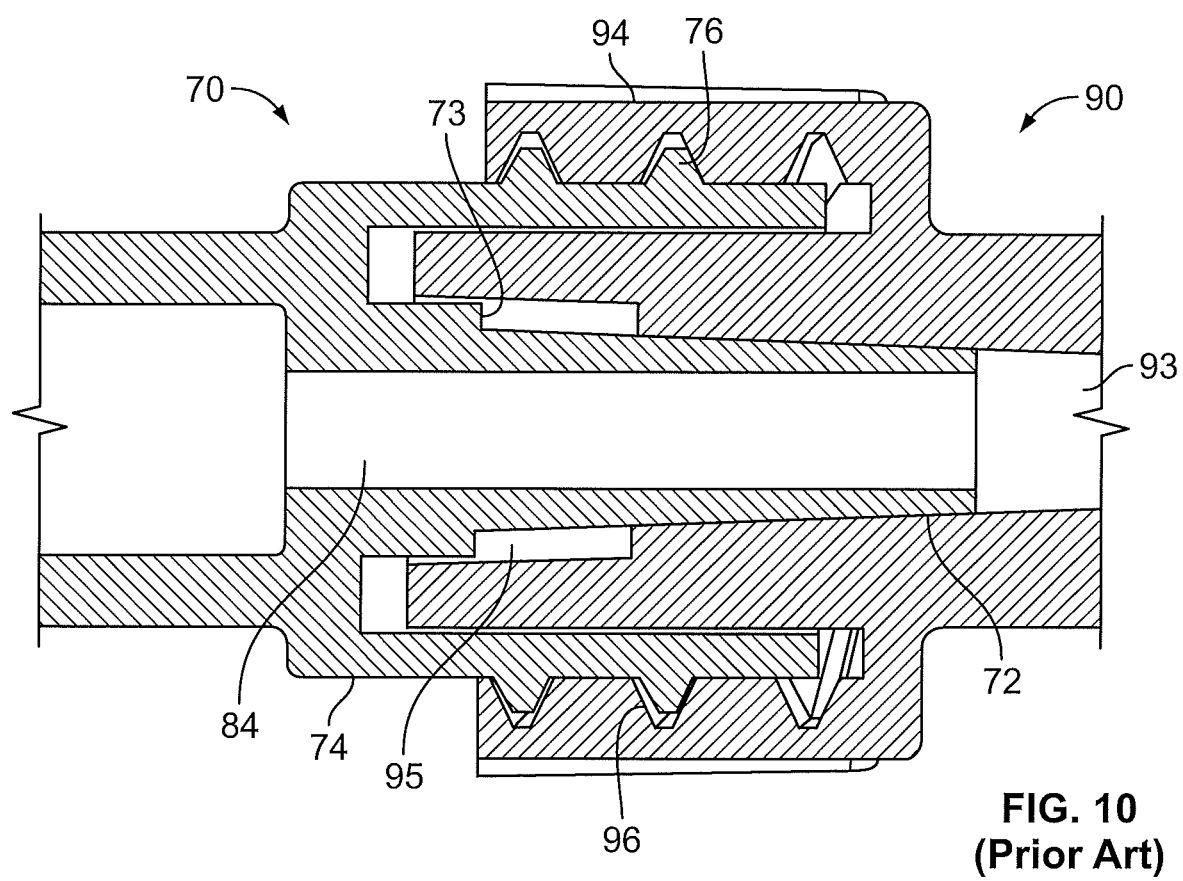
FIG. 10 is a partial cross sectional view of the connector of FIGS. 6 and 7 joined to the connector of FIGS. 8 and 9.

The exterior of the collar 142 of the connector 134 of FIG. 12 may be provided with raised ribs 162 for gripping and turning the adapter while connector 134 is being joined to a compatible connector. The exterior of the collar 154 of the connector 136 of FIG. 10 may be provided with raised ribs 164 for gripping and turning the adapter while connector 136 is being joined to a compatible connector.

Figure 3:
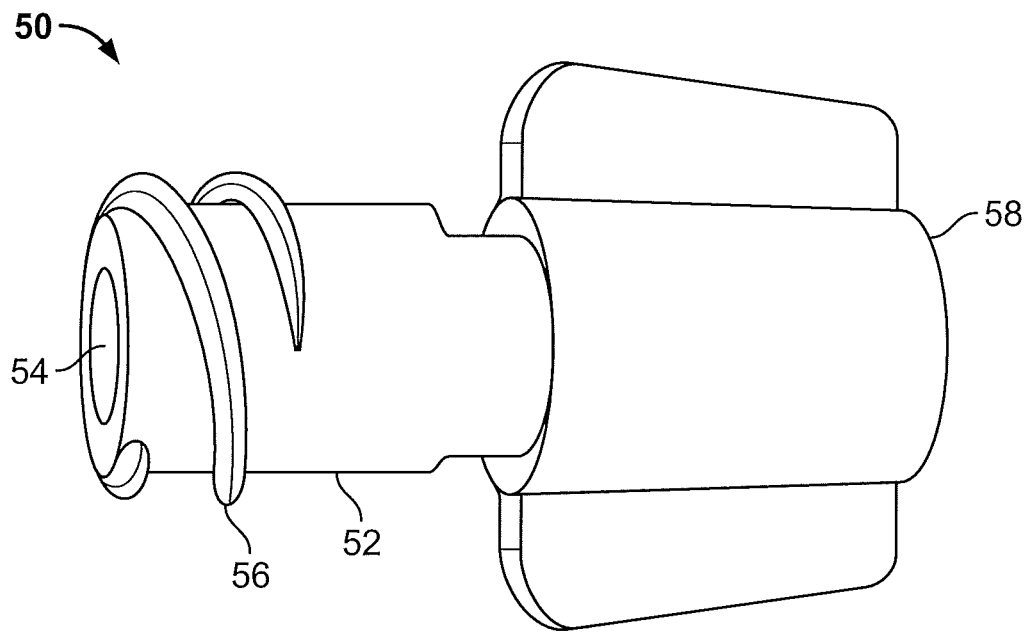
FIG. 3 is a perspective view of an ISO 594 female Luer connector.
Figure 4:
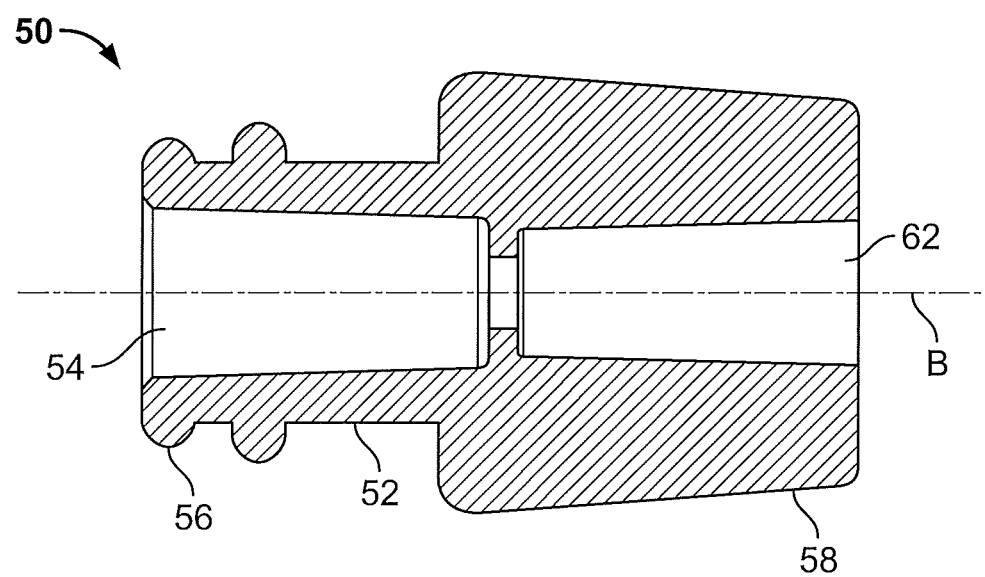
FIG. 4 is a cross sectional view of the connector of FIG. 3 with the cutting plane parallel to, and passing through, the longitudinal axis of the connector, indicated at B.
Figure 13:
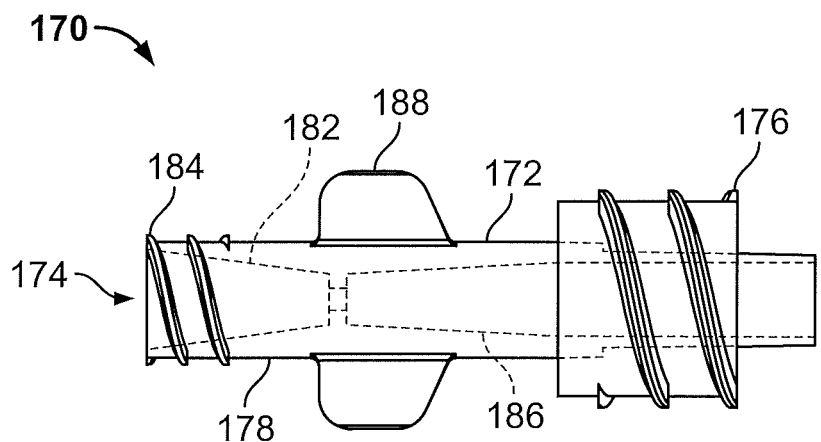
FIG. 13 is a side elevational view of a third embodiment of the adapter of the disclosure.

A third embodiment of the adapter of the disclosure is indicated in general at 170 in FIG. 13. The adapter includes a fluid flow conduit 172 having an ISO 594 female Luer connector, indicated in general at 174, positioned on one end and an ISO 18250 male Luer connector, indicated at 176, positioned on the other end. The ISO 594 female Luer connector, as described above with reference to FIGS. 3 and 4, includes a cylindrical portion 178 having a socket 182 that features a Luer taper and that receives the conical member of an ISO 594 male Luer connector (32 of FIGS. 1 and 2). The exterior surface of the cylindrical portion is provided with threads 184 that are compatible with the threads of an ISO 594 male Luer connector (36 of FIGS. 1 and 2).

The ISO 18250 male Luer connector 176 has the same construction as described above with reference to FIG. 11

A central fluid flow lumen 186 extends through the fluid flow conduit 172 and the connectors 174 and 176. As a result, the adapter 170 may be used to join a medical component featuring an ISO 594 male Luer connector (which is joined to connector 174) to a separate medical component featuring an ISO 18250 female Luer connector (which is joined to connector 176) so that the two components are in fluid communication with one another.

One or more wings 188 are preferably provided on the exterior surface of the fluid flow conduit 172 and may be received between a user's finger tips for gripping and turning while the connectors 174 or 176 are being joined to a compatible connector.

Figure 14:
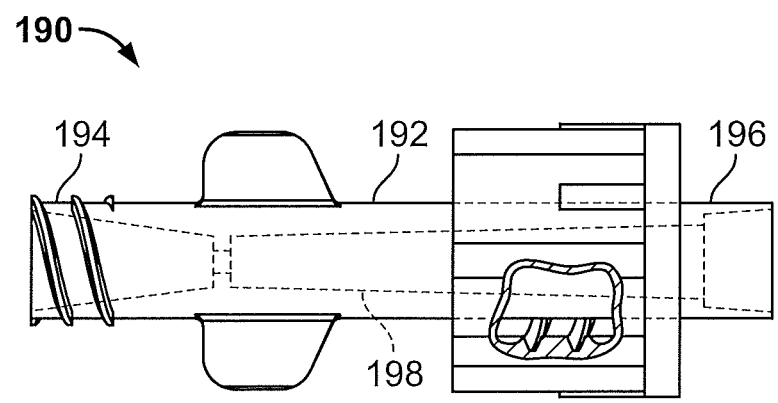
FIG. 14 is a partially broken away, side elevational view of a fourth embodiment of the adapter of the disclosure.

A fourth embodiment of the adapter of the disclosure is indicated in general at 190 in FIG. 14. The adapter includes a fluid flow conduit 192 having an ISO 594 female Luer connector, indicated at 194, positioned on one end and an ISO 18250 female Luer connector, indicated at 196, positioned on the other end. The ISO 594 female Luer connector 194 has the same construction as described above with reference to FIG. 13, while the ISO 18250 female Luer connector 196 has the same construction as described above with reference to FIG. 12.

A central fluid flow lumen 198 extends through the fluid flow conduit 192 and the connectors 194 and 196. As a result, the adapter 190 may be used to join a medical component featuring an ISO 594 male Luer connector (which is joined to connector 194) to a separate medical component featuring an ISO 18250 male Luer connector (which is joined to connector 196) so that the two components are in fluid communication with one another.

Figure 15:
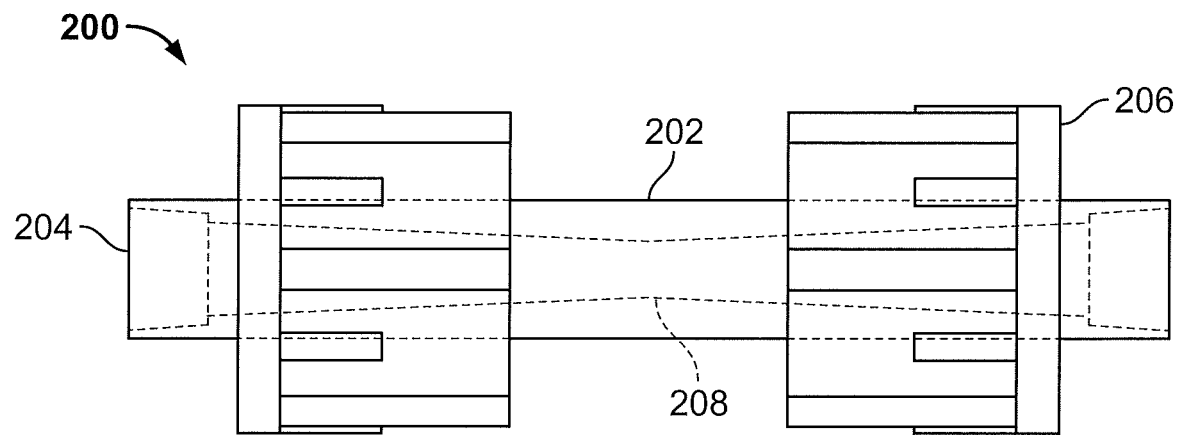
FIG. 15 is a side elevational view of a fifth embodiment of the adapter of the disclosure.

A fifth embodiment of the adapter of the disclosure is indicated in general at 200 in FIG. 15. The adapter includes a fluid flow conduit 202 having a first ISO 18250 female Luer connector, indicated at 204, positioned on one end and a second ISO 18250 female Luer connector, indicated at 206, positioned on the other end. The ISO 18250 female Luer connectors 204 and 206 have the same construction as described above with reference to FIG. 12.

A central fluid flow lumen 208 extends through the fluid flow conduit 202 and the connectors 204 and 206. As a result, the adapter 200 may be used to join medical components featuring ISO 18250 male Luer connectors so as to be in fluid communication with one another.

Figure 16:
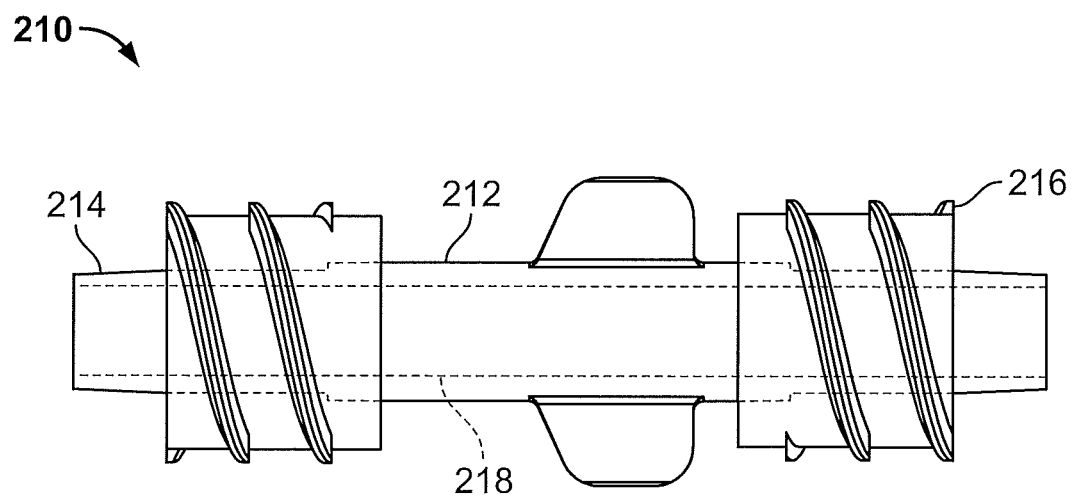
FIG. 16 is a side elevational view of a sixth embodiment of the adapter of the disclosure.

A sixth embodiment of the adapter of the disclosure is indicated in general at 210 in FIG. 16. The adapter includes a fluid flow conduit 212 having a first ISO 18250 male Luer connector, indicated at 214, positioned on one end and a second ISO 18250 male Luer connector, indicated at 216, positioned on the other end. The ISO 18250 female Luer connectors 214 and 216 have the same construction as described above with reference to FIG. 11.

A central fluid flow lumen 218 extends through the fluid flow conduit 212 and the connectors 214 and 216. As a result, the adapter 210 may be used to join medical components featuring ISO 18250 female Luer connectors so as to be in fluid communication with one another.

Figure 17:
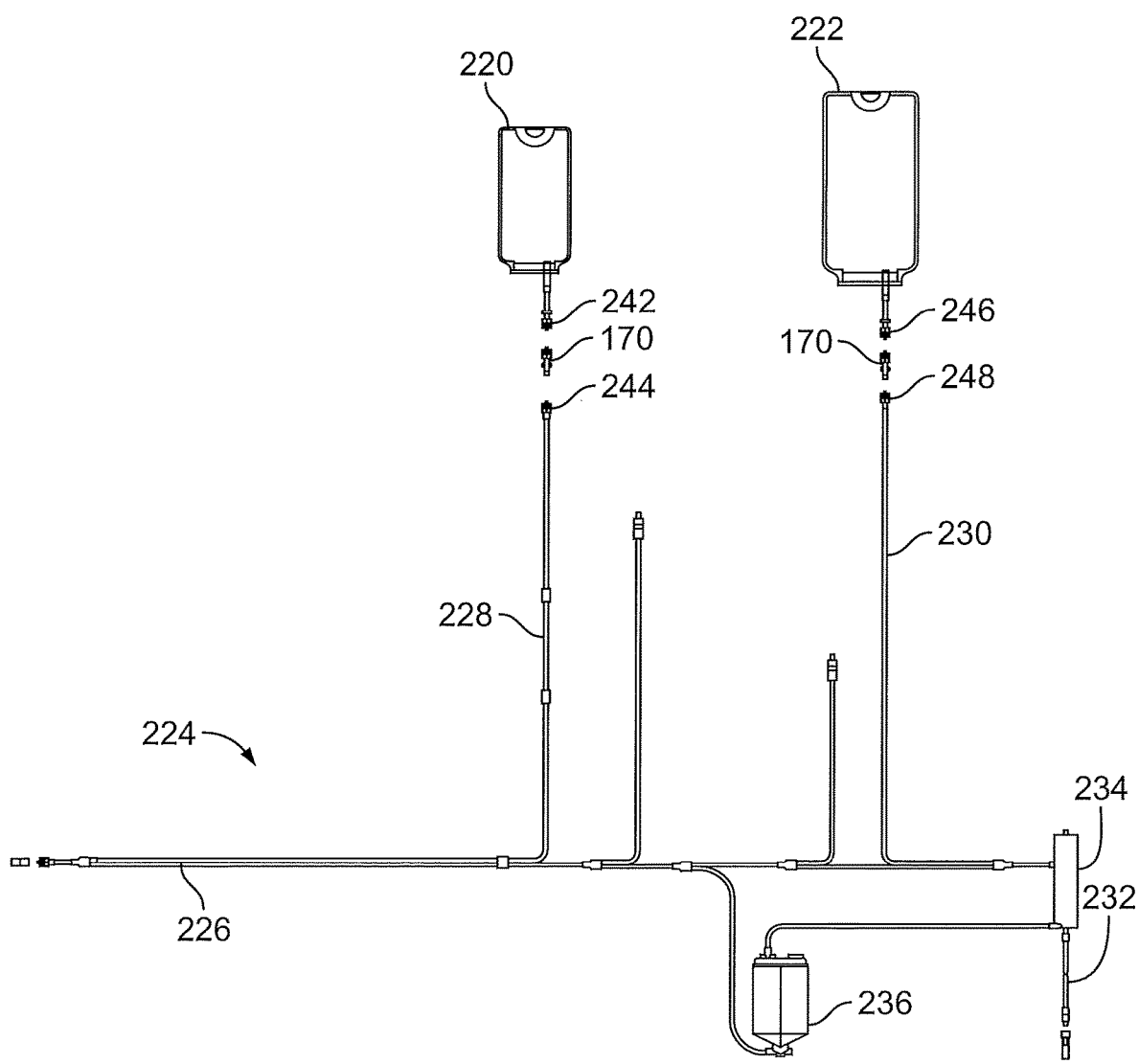
FIG. 17 is a schematic of a medical fluid flow system, e.g., an apheresis system, illustrating use of an embodiment of the adapter of the disclosure.

An example of use of adapters of the disclosure in connecting solution bags 220 and 222 to a disposable fluid flow system, such as an apheresis set, indicated in general at 224, is presented in FIG. 17. As is known in the art, the apheresis set includes a donor line 226, an anticoagulant (AC) line 228, a saline line 230 and a plasma line 232. A spinner device 234 (for separating plasma from whole blood) and a reservoir 236 are also included and connected to the donor and plasma lines so that blood may be received from a patient and processed with the spinner device 234 so that processed blood is directed to the reservoir 236 while plasma is directed through the plasma line 232. The processed blood in the reservoir may be returned to the donor/patient.

Figure 5:
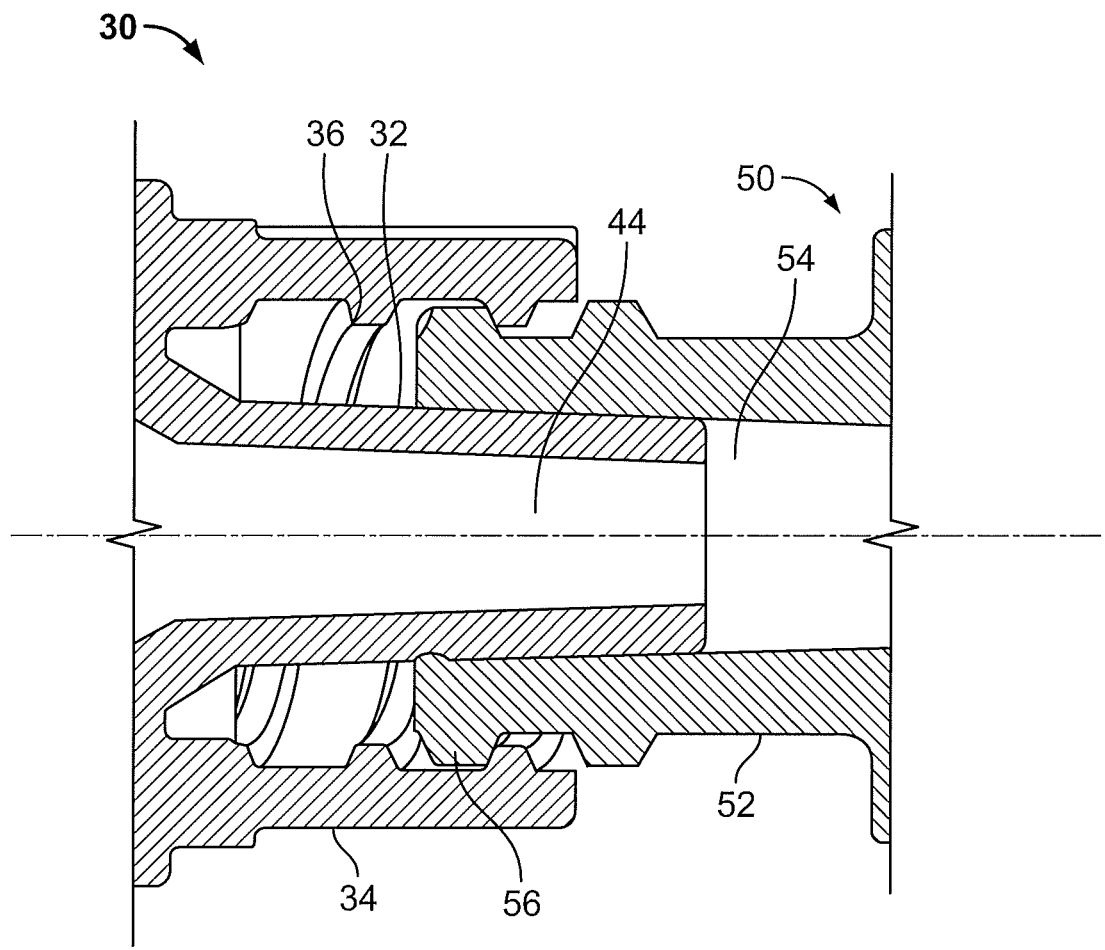
FIG. 5 is a partial cross sectional view of the connector of FIGS. 1 and 2 joined to the connector of FIGS. 3 and 4.

In the example presented in FIG. 17, for purposes of non-exclusive illustration, the AC solution bag features an ISO 18250 female Luer connector 242 while the AC line 228 features an ISO 594 male Luer connector 244. As a result, the adapter 170 of FIG. 13 may be used to join the bag 220 to the AC line 228 of the disposable apheresis set, where the joined ISO 18250 connector 242 and corresponding connector of adapter 170 appear as in FIG. 10 while the joined ISO 594 connector 244 and corresponding connector of adapter 170 appear as in FIG. 5.

Saline solution bag 222 of FIG. 17 features an ISO 18250 male Luer connector 246 while the saline line 230 features an ISO 594 male Luer connector 248. As a result, the adapter 190 of FIG. 14 may be used to join the bag 222 to the saline line 230 of the disposable apheresis set, where the joined ISO 18250 connector 246 and corresponding connector of adapter 170 appear as in FIG. 10 while the joined ISO 594 connector 248 and corresponding connector of adapter 170 appear as in FIG. 5.

Alternative embodiments of the adapter of the disclosure provide a combination closure cap, which improves efficiency and eliminates the need for multiple connector caps. As an example, an apheresis disposable set may have one line with and ISO 18250 female Luer connector and another line with an ISO 594 male Luer connector. When the two lines are not connected to anything, they will need to be capped. Instead of having a separate ISO 18250 female Luer connector and ISO 594 male Luer connector caps, a single combination cap adapter may be used. Examples of such embodiments are presented in FIGS. 18-24. Alternatively, the adapter may be used as a cap on a single fluid flow component without another component being attached.

Figure 18:
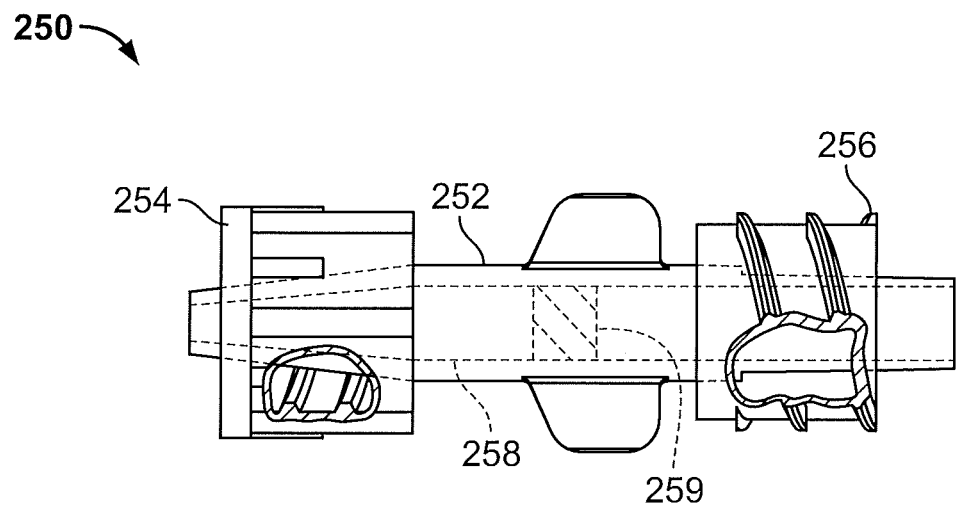
FIG. 18 is a partially broken away, side elevational view of a seventh embodiment of the adapter of the disclosure for sealing or capping a connector.

A seventh embodiment of the adapter of the disclosure is indicated in general at 250 in FIG. 18. The adapter includes a conduit 252 having an ISO 594 male Luer connector, indicated at 254, positioned on one end and an ISO 18250 male Luer connector, indicated at 256, positioned on the other end. The ISO 594 male Luer connector 254 and the ISO 18250 male Luer connector 256 have the same construction as described above with reference to FIG. 11.

In contrast to the embodiments of the adapter described previously, the central lumen 258 running through the conduit 252 is provided with an obstruction 259 which blocks fluid flow between the ends of the adapter. Alternatively, the central lumen may be eliminated entirely, since fluid flow between the connected medical components is not desired.

Figure 19:
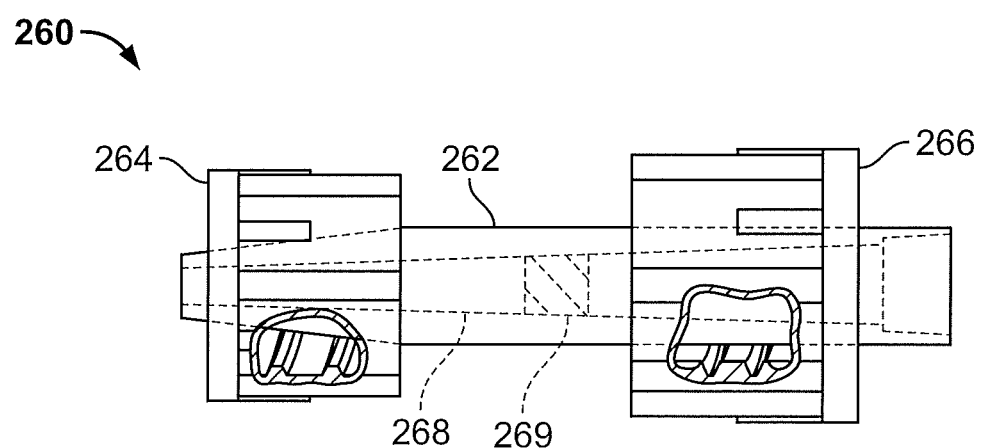
FIG. 19 is a partially broken away, side elevational view of an eighth embodiment of the adapter of the disclosure for sealing or capping a connector.

An eighth embodiment of the adapter of the disclosure is indicated in general at 260 in FIG. 19. The adapter includes a conduit 262 having an ISO 594 male Luer connector, indicated at 264, positioned on one end and an ISO 18250 female Luer connector, indicated at 266, positioned on the other end. The ISO 594 male Luer connector 264 and the ISO 18250 female Luer connector 266 have the same construction as described above with reference to FIG. 12.

The central lumen 268 running through the conduit 262 is provided with an obstruction 269 which blocks fluid flow between the ends of the adapter. Alternatively, the central lumen may be eliminated entirely, since fluid flow between the connected medical components is not desired.

Figure 20:
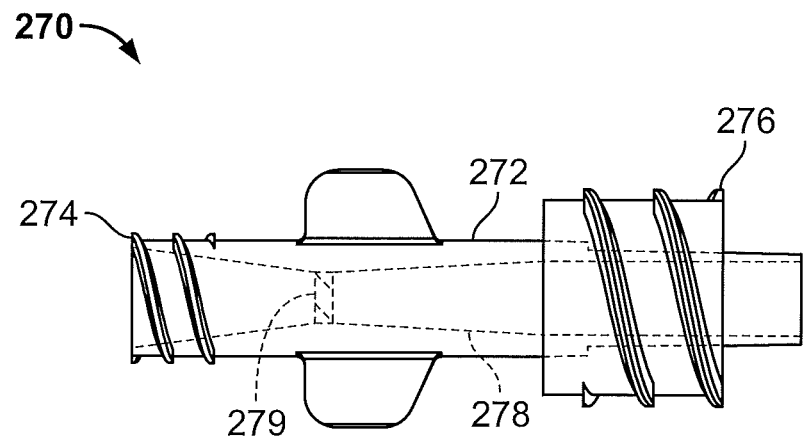
FIG. 20 is a side elevational view of a ninth embodiment of the adapter of the disclosure for sealing or capping a connector.

A ninth embodiment of the adapter of the disclosure is indicated in general at 270 in FIG. 20. The adapter includes a conduit 272 having an ISO 594 female Luer connector, indicated at 274, positioned on one end and an ISO 18250 male Luer connector, indicated at 276, positioned on the other end. The ISO 594 female Luer connector 274 and the ISO 18250 male Luer connector 276 have the same construction as described above with reference to FIG. 13.

The central lumen 278 running through the conduit 272 is provided with an obstruction 279 which blocks fluid flow between the ends of the adapter. Alternatively, the central lumen may be eliminated entirely, since fluid flow between the connected medical components is not desired.

Figure 21:
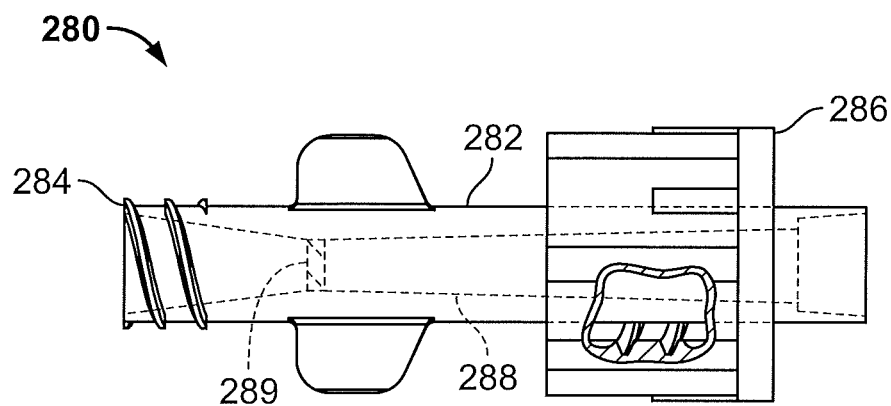
FIG. 21 is a partially broken away, side elevational view of a tenth embodiment of the adapter of the disclosure for sealing or capping a connector.

A tenth embodiment of the adapter of the disclosure is indicated in general at 280 in FIG. 21. The adapter includes a conduit 282 having an ISO 594 female Luer connector, indicated at 284, positioned on one end and an ISO 18250 female Luer connector, indicated at 286, positioned on the other end. The ISO 594 female Luer connector 284 and the ISO 18250 female Luer connector 286 have the same construction as described above with reference to FIG. 14.

The central lumen 288 running through the conduit 282 is provided with an obstruction 289 which blocks fluid flow between the ends of the adapter. Alternatively, the central lumen may be eliminated entirely, since fluid flow between the connected medical components is not desired.

Figure 22:
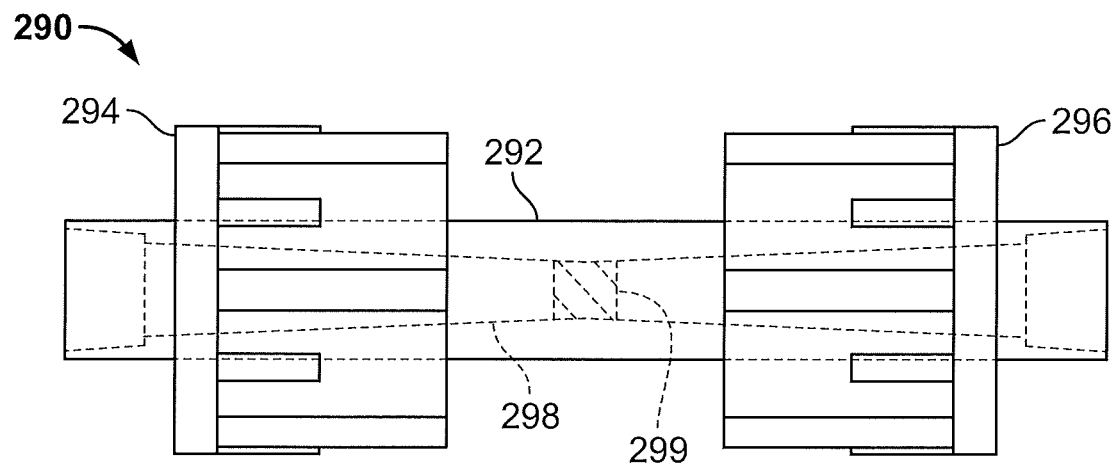
FIG. 22 is a side elevational view of an eleventh embodiment of the adapter of the disclosure for sealing or capping a connector.

An eleventh embodiment of the adapter of the disclosure is indicated in general at 290 in FIG. 22. The adapter includes a conduit 292 having a first ISO 18250 female Luer connector, indicated at 294, positioned on one end and a second ISO 18250 female Luer connector, indicated at 296, positioned on the other end. The ISO 18250 female Luer connectors 284 and 286 have the same construction as described above with reference to FIG. 12.

The central lumen 298 running through the conduit 292 is provided with an obstruction 299 which blocks fluid flow between the ends of the adapter. Alternatively, the central lumen may be eliminated entirely, since fluid flow between the connected medical components is not desired.

Figure 23:
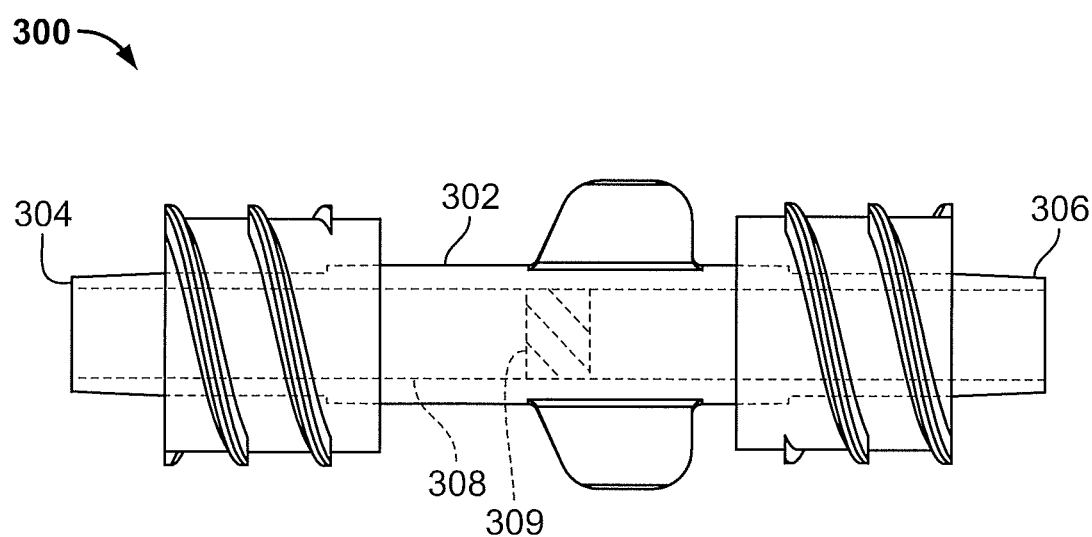
FIG. 23 is a side elevational view of a twelfth embodiment of the adapter of the disclosure for sealing or capping a connector.

A twelfth embodiment of the adapter of the disclosure is indicated in general at 300 in FIG. 23. The adapter includes a conduit 302 having a first ISO 18250 male Luer connector, indicated at 304, positioned on one end and a second ISO 18250 male Luer connector, indicated at 306, positioned on the other end. The ISO 18250 male Luer connectors 304 and 306 have the same construction as described above with reference to FIG. 11.

The central lumen 308 running through the conduit 302 is provided with an obstruction 399 which blocks fluid flow between the ends of the adapter. Alternatively, the central lumen may be eliminated entirely, since fluid flow between the connected medical components is not desired.

Figure 24:
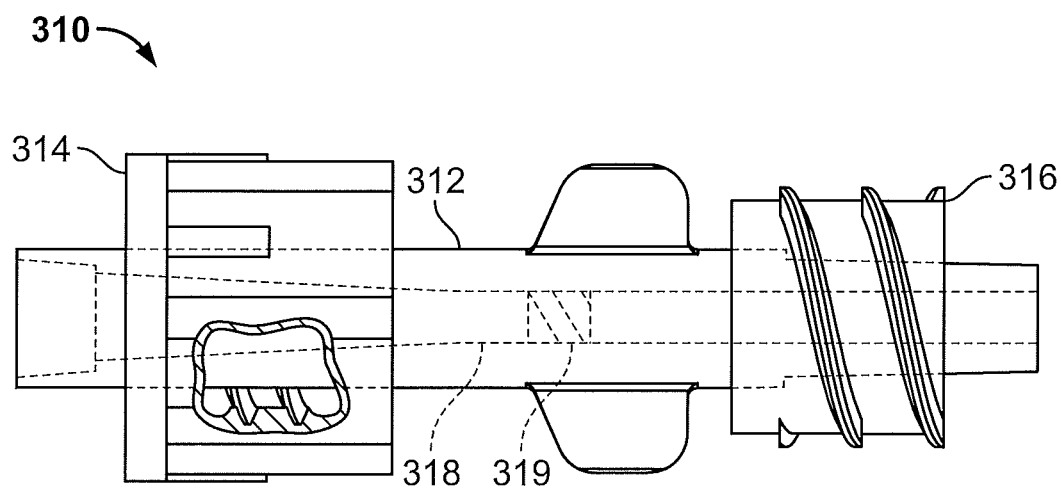
FIG. 24 is a partially broken away, side elevational view of a thirteenth embodiment of the adapter of the disclosure for sealing or capping a connector.

A thirteenth embodiment of the adapter of the disclosure is indicated in general at 310 in FIG. 24. The adapter includes a conduit 312 having an ISO 18250 female Luer connector, indicated at 314, positioned on one end and an ISO 18250 male Luer connector, indicated at 316, positioned on the other end. The ISO 18250 female Luer connector 314 and the ISO 18250 male Luer connector 316 have the same construction as described above with reference to FIGS. 11 and 12.

The central lumen 318 running through the conduit 312 is provided with an obstruction 319 which blocks fluid flow between the ends of the adapter. Alternatively, the central lumen may be eliminated entirely, since fluid flow between the connected medical components is not desired.

Figure 25:
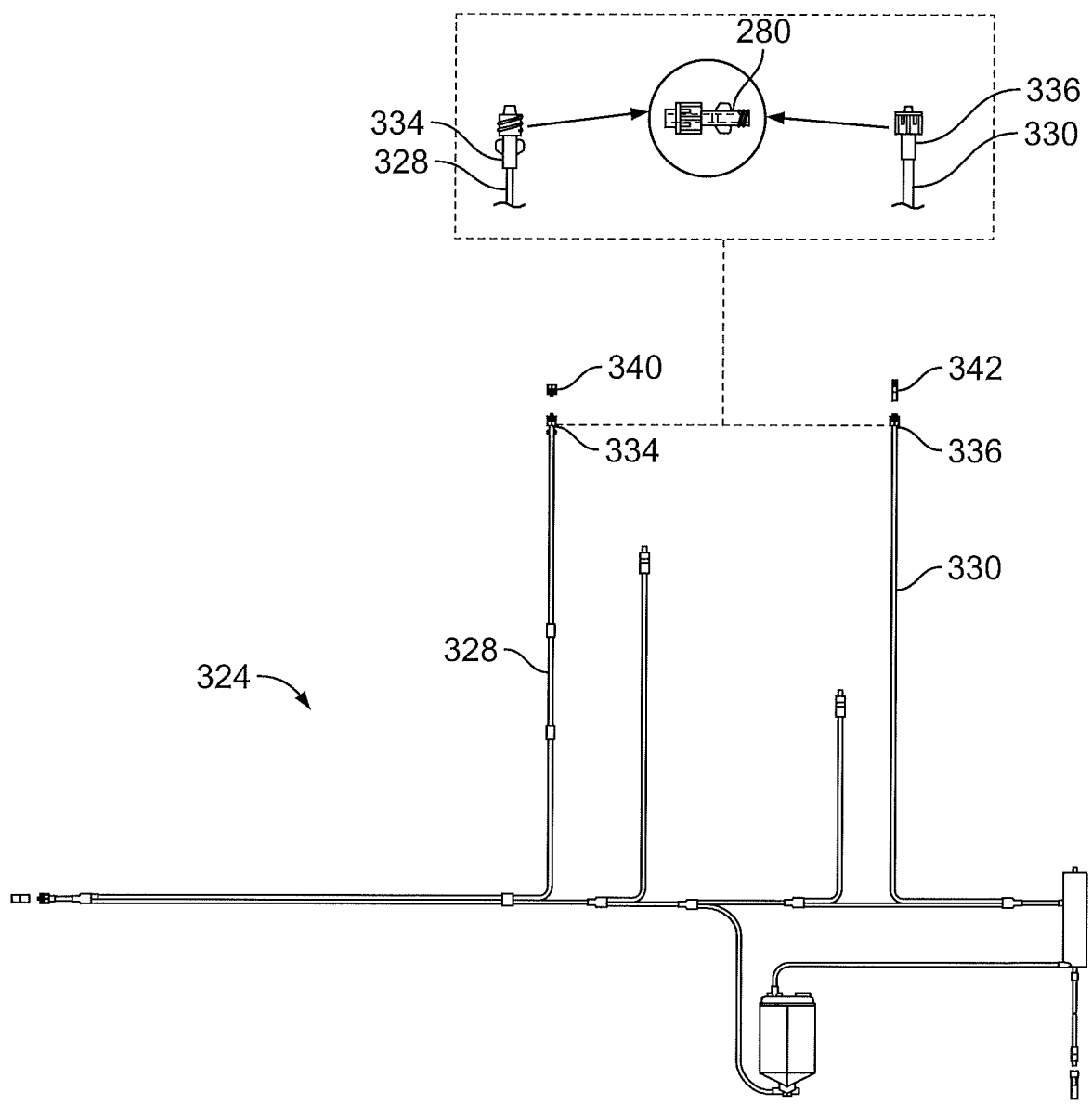
FIG. 25 is a schematic of a disposable medical fluid flow system, e.g. an apheresis set, illustrating use of one of the embodiments of the adapter for sealing or capping a connector.

An example of use of adapters of FIGS. 18-24 with the disposable apheresis set, indicated in general at 324, is presented in FIG. 25. The disposable apheresis set features the same construction as the set 224 of FIG. 17 with the exception that AC line 328 features an ISO 18250 male Luer connector 334. The saline line 330 features an ISO 594 male Luer connector 336. Therefore, the adapter 280 of FIG. 21 may be used to cap both AC line 328 and saline line 330 simultaneously. As a result the individual caps 340 and 342 (of two different types) are not needed. Alternatively, if desired, two separate adapters may be used—one for each apheresis set connector.

ASPECTS

Aspect 1. An adapter for making a fluid connection between first and second medical fluid flow components in which the first medical fluid flow component includes a first male Luer or female Luer connector of a first configuration, and the second medical fluid flow component includes a second male Luer or female Luer connector of a second configuration that is not compatible with the first configuration, the adapter comprising: a fluid flow conduit including a first end and a second end and a fluid flow lumen extending between the first and second ends; a first adapter connector at the first end of said conduit, said first adapter connector being a male Luer or female Luer having a first configuration compatible with the first medical fluid flow component connector; and a second adapter connector at the second end of said conduit, said second adapter connector being a male Luer or female Luer having a second configuration compatible with the second medical fluid flow component connector.

Aspect 2. The adapter of Aspect 1 wherein the first adapter connector is compliant with a first technical standard and the second adapter connector is compliant with a second and different technical standard.

Aspect 3. The adapter of Aspect 2 wherein the first technical standard is ISO 594 and the second technical standard is ISO 18250.

Aspect 4. The adapter of any one of Aspects 1-3 wherein the first adapter connector is a male Luer connector and the second adapter connector is a female Luer connector, or wherein the first adapter connector is a female Luer connector and the second adapter connector is a male Luer connector.

Aspect 5. The adapter of Aspect 2 in which the first adapter connector is a male Luer connector compliant with the first technical standard and the second adapter connector is a male Luer connector compliant with the second technical standard.

Aspect 6. The adapter of Aspect 2 in which the first adapter connector is a male Luer connector compliant with the first technical standard and the second adapter connector is a female Luer connector compliant with the second technical standard.

Aspect 7. The adapter of Aspect 2 in which the first adapter connector is a female Luer connector compliant with the first technical standard and the second adapter connector is a male Luer connector compliant with the second technical standard.

Aspect 8. The adapter of Aspect 2 in which the first adapter connector is a female Luer connector compliant with the first technical standard and the second adapter connector is a female Luer connector compliant with the second technical standard.

Aspect 9. The adapter of any one of Aspects 1-8 further comprising an obstruction in the lumen blocking fluid flow between the first and second ends of the adapter.

Aspect 10. The adapter of any one of Aspects 1-9 wherein the first adapter connector includes a surface having raised gripping ridges.

Aspect 11. The adapter of any one of Aspects 1-9 wherein the second adapter connector includes a surface having raised gripping ridges.

Aspect 12. The adapter of any one of Aspects 1-11 wherein the fluid flow conduit includes a wing adapted to be engaged by a user's fingers when turning the adapter.

Aspect 13. The adapter of any one of Aspects 1-12 wherein the first or second adapter connector includes a collar.

Aspect 14. The adapter of Aspect 13 wherein the collar includes an internal surface having threads.

Aspect 15. The adapter of Aspect 13 wherein the collar includes an external surface having threads.

Aspect 16. The adapter of Aspects 1-12 wherein the first adapter connector includes a first collar and the second adapter connector includes a second collar.

Aspect 17. The adapter of Aspect 16 wherein the first collar includes an internal surface with a first set of threads and the second collar includes an internal surface with a second set of threads.

Aspect 18. The adapter of Aspect 16 wherein the first collar includes an internal surface with a first set of threads and the second collar includes an external surface with a second set of threads.

Aspect 19. The adapter of Aspects 1-12 wherein the first or second adapter connector includes an external surface having threads.

Aspect 20. The adapter of any one of Aspects 1-12 wherein the adapter is integrally formed of a substantially rigid plastic material.

Aspect 21. A cap for closing fluid flow access to a medical fluid flow component having a male or female Luer connector of a first configuration or a second configuration or for making a closed fluid flow blocking connection between first and second medical fluid flow components in which the first medical fluid flow component includes a first male Luer or female Luer connector of a first configuration, and the second medical fluid flow component includes a second male Luer or female Luer connector of a second configuration that is not compatible with the first configuration, the cap comprising: a member including a first end and a second end; a first cap connector at the first end of said member, said first cap connector being a male Luer or female Luer having a first configuration compatible with the first medical fluid flow component connector; and a second cap connector at the second end of said member, said second cap connector being a male Luer or female Luer having a second configuration compatible with the second medical fluid flow component connector.

Aspect 22. The cap of Aspect 21 wherein the first cap connector is compliant with a first technical standard and the second cap connector is compliant with a second and different technical standard.

Aspect 23. The cap of Aspect 22 wherein the first technical standard is ISO 594 and the second technical standard is ISO 18250.

Aspect 24. The cap of any one of Aspects 21-23 wherein the first cap connector is a male Luer connector and the second cap connector is a female Luer connector, or wherein the first cap connector is a female Luer connector and the second cap connector is a male Luer connector.

Aspect 25. The cap of Aspect 22 in which the first cap connector is a male Luer connector compliant with the first technical standard and the second cap connector is a male Luer connector compliant with the second technical standard.

Aspect 26. The cap of Aspect 22 in which the first cap connector is a male Luer connector compliant with the first technical standard and the second cap connector is a female Luer connector compliant with the second technical standard.

Aspect 27. The cap of Aspect 22 in which the first cap connector is a female Luer connector compliant with the first technical standard and the second cap connector is a male Luer connector compliant with the second technical standard.

Aspect 28. The cap of Aspect 22 in which the first cap connector is a female Luer connector compliant with the first technical standard and the second cap connector is a female Luer connector compliant with the second technical standard.

Aspect 29. The cap of any one of Aspects 21-28 further comprising an obstruction in the lumen blocking fluid flow between the first and second ends of the cap.

Aspect 30. The cap of any one of Aspects 21-29 wherein the first cap connector includes a surface having raised gripping ridges.

Aspect 31. The cap of any one of Aspects 21-29 wherein the second cap connector includes a surface having raised gripping ridges.

Aspect 32. The cap of any one of Aspects 21-31 wherein the fluid flow conduit includes a wing adapted to be engaged by a user's fingers when turning the cap.

Aspect 33. The cap of any one of Aspects 21-32 wherein the first or second cap connector includes a collar.

Aspect 34. The cap of Aspect 33 wherein the collar includes an internal surface having threads.

Aspect 35. The cap of Aspect 33 wherein the collar includes an external surface having threads.

Aspect 36. The cap of Aspects 21-32 wherein the first cap connector includes a first collar and the second cap connector includes a second collar.

Aspect 37. The cap of Aspect 36 wherein the first collar includes an internal surface with a first set of threads and the second collar includes an internal surface with a second set of threads.

Aspect 38. The cap of Aspect 36 wherein the first collar includes an internal surface with a first set of threads and the second collar includes an external surface with a second set of threads.

Aspect 39. The cap of Aspects 21-32 wherein the first or second cap connector includes an external surface having threads.

Aspect 40. The cap of any one of Aspects 21-32 wherein the cap is integrally formed of a substantially rigid plastic material.

Aspect 41. An adapter for making a fluid connection between first and second apheresis fluid flow components in which the first apheresis fluid flow component includes a first male Luer or female Luer connector that is compliant with an apheresis connector technical standard, and the second apheresis fluid flow component includes a second male Luer or female Luer connector that is compliant with the apheresis connector technical standard, the adapter comprising: a fluid flow conduit including a first end and a second end and a fluid flow lumen extending between the first and second ends; a first adapter connector at the first end of said conduit, said first adapter connector being a male Luer or female Luer having a first configuration compatible with the first apheresis fluid flow component connector; and a second adapter connector at the second end of said conduit, said second adapter connector being a male Luer or female Luer having a second configuration compatible with the second apheresis fluid flow component connector.

Aspect 42. The adapter of Aspect 41 wherein the second male Luer or female Luer connector is not compatible with the first male Luer or female Luer connector.

Aspect 43. The adapter of Aspect 41 or 42 wherein the apheresis connector technical standard is ISO 18250.

Aspect 44. The adapter of any one of Aspects 41-43 wherein the first and second adapter connectors are both male Luer connectors.

Aspect 45. The adapter of any one of Aspects 41-43 wherein the first and second adapter connectors are both female Luer connectors.

Aspect 46. The adapter of any one of Aspects 41-43 wherein first adapter connector includes a first collar and the second adapter connector includes a second collar.

Aspect 47. The adapter of Aspect 46 wherein the first and second collars include internal surfaces having threads.

Aspect 48. The adapter of Aspect 46 wherein the first and second collars include external surfaces having threads.

Aspect 49. The adapter of Aspect 46 wherein the first collar includes an internal surface having threads and the second collar includes an external surface having threads.

Aspect 50. The adapter of any one of Aspects 41-49 further comprising an obstruction in the lumen blocking fluid flow between the first and second ends of the adapter.

Aspect 51. A cap for closing fluid flow access to an apheresis fluid flow component having a male or female connector of a first configuration or a second configuration, or for and making a closed fluid flow blocking connection between first and second apheresis fluid flow components in which the first apheresis fluid flow component includes a first male Luer or female Luer connector that is compliant with an apheresis connector technical standard, and the second apheresis fluid flow component includes a second male Luer or female Luer connector that is compliant with the apheresis connector technical standard, the cap comprising: a member including a first end and a second end; a first adapter connector at the first end of said member, said first adapter connector being a male Luer or female Luer having a first configuration compatible with the first apheresis fluid flow component connector; and a second adapter connector at the second end of said member, said second adapter connector being a male Luer or female Luer having a second configuration compatible with the second apheresis fluid flow component connector.

Aspect 52. The cap of Aspect 51 wherein the second male Luer or female Luer connector is not compatible with the first male Luer or female Luer connector.

Aspect 53. The adapter of Aspect 51 or 52 wherein the apheresis connector technical standard is ISO 18250.

Aspect 54. The adapter of any one of Aspects 51-53 wherein the first and second adapter connectors are both male Luer connectors.

Aspect 55. The adapter of any one of Aspects 51-53 wherein the first and second adapter connectors are both female Luer connectors.

Aspect 56. The adapter of any one of Aspects 51-53 wherein first adapter connector includes a first collar and the second adapter connector includes a second collar.

Aspect 57. The adapter of Aspect 56 wherein the first and second collars include internal surfaces having threads.

Aspect 58. The adapter of Aspect 56 wherein the first and second collars include external surfaces having threads.

Aspect 59. The adapter of Aspect 56 wherein the first collar includes an internal surface having threads and the second collar includes an external surface having threads.

Aspect 60. The adapter of any one of Aspects 51-59 wherein the adapter is integrally formed of a substantially rigid plastic material.

Aspect 61. A method for making a fluid connection between first and second medical fluid flow components in which the first medical fluid flow component includes a first male Luer or female Luer connector of a first configuration, and the second medical fluid flow component includes a second male Luer or female Luer connector of a second configuration that is not compatible with the first configuration, the method comprising the steps of: connecting the first medical fluid flow component connector to a first adapter male or female connector having a configuration compatible with the first medical fluid flow connector; and connecting the second medical fluid flow component connector to a second adapter male or female connector having a configuration compatible with the second medical fluid flow connector.

Aspect 62. A method for closing fluid flow access to a medical fluid flow component having a male or female Luer connector of a first configuration or a second configuration, or for making a closed fluid flow blocking connection between first and second medical fluid flow components in which the first medical fluid flow component includes a first male Luer or female Luer connector of a first configuration, and the second medical fluid flow component includes a second male Luer or female Luer connector of a second configuration that is not compatible with the first configuration, the method comprising the steps of: connecting the first medical fluid flow component connector to a first cap male or female connector having a configuration compatible with the first medical fluid flow connector; and connecting the second medical fluid flow component connector to a second cap male or female connector having a configuration compatible with the second medical fluid flow connector.

Aspect 63. A medical fluid flow system comprising: first and second medical fluid flow components in which the first medical fluid flow component includes a first male Luer or female Luer connector of a first configuration, and the second medical fluid flow component includes a second male Luer or female Luer connector of a second configuration that is not compatible with the first configuration; an adapter making a fluid connection between first and second medical fluid flow components including: a fluid flow conduit including a first end and a second end and a fluid flow lumen extending between the first and second ends; a first adapter connector at the first end of said conduit, said first adapter connector being a male Luer or female Luer having a first configuration compatible with the first medical fluid flow component connector, and a second adapter connector at the second end of said conduit, said second adapter connector being a male Luer or female Luer having a second configuration compatible with the second medical fluid flow component connector.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. An adapter for making a fluid connection between first and second medical fluid flow components in which the first medical fluid flow component includes a first male Luer or female Luer connector of a first configuration, and the second medical fluid flow component includes a second male Luer or female Luer connector of a second configuration that is not compatible with the first configuration, the adapter comprising:
   a. a rigid fluid flow conduit including a first end and a second end and a fluid flow lumen extending between the first and second ends, said fluid flow conduit including a wing fixedly secured to the fluid flow conduit and adapted to be engaged by a user's fingers when turning the adapter and wherein said fluid flow lumen is configured so that a stream of liquid flows through, and is in fluid communication with, the fluid flow lumen when the adapter is connected between first and second medical fluid flow components and is configured so that liquid flows from the first medical fluid flow component to the second medical fluid flow component;
   b. a first adapter connector positioned at the first end of said fluid flow conduit, said first adapter connector having a first set of threads and also having a first collar fixedly secured to and radially spaced from the fluid flow conduit and being a male Luer or female Luer having a first configuration configured to be releasably connected with the first medical fluid flow component connector by the first set of threads;
   c. a second adapter connector positioned at the second end of said fluid flow conduit so as to be spaced from the first adapter connector by the fluid flow lumen, said second adapter connector having a second set of threads and also having a second collar fixedly secured to and radially spaced from the fluid flow conduit and being a male Luer or female Luer having a second configuration configured to be releasably connected with the second medical fluid flow component connector by the second set of threads; and
   d. a pair of wings fixedly secured to the fluid flow conduit between and spaced from both the first collar of the first adapter connector and the second collar of the second adapter connector.

2. The adapter of claim 1 wherein the first adapter connector is a male Luer connector and the second adapter connector is a female Luer connector, or wherein the first adapter connector is a female Luer connector and the second adapter connector is a male Luer connector.

3. The adapter of claim 1 further comprising an obstruction in the fluid flow lumen blocking fluid flow between the first and second ends of the adapter, said obstruction being positioned radially inward of the pair of wings.

4. The adapter of claim 1 wherein the first adapter connector includes a surface having raised gripping ridges.

5. The adapter of claim 4 wherein the second adapter connector includes a surface having raised gripping ridges.

6. The adapter of claim 1 wherein the first or the second collar includes an internal surface having the first or second set of threads.

7. The adapter of claim 1 wherein the first or the second collar includes an external surface having the first or second set of threads.

8. The adapter of claim 1 wherein the first collar includes an internal surface with the first set of threads and the second collar includes an internal surface with the second set of threads.

9. The adapter of claim 1 wherein the first collar includes an internal surface with the first set of threads and the second collar includes an external surface with the second set of threads.

10. The adapter of claim 1 wherein the first or second adapter connector includes an external surface having the first or second set of threads.

11. A method for making a fluid connection between first and second medical fluid flow components in which the first medical fluid flow component includes a first male Luer or female Luer connector of a first configuration, and the second medical fluid flow component includes a second male Luer or female Luer connector of a second configuration that is not compatible with the first configuration, the method comprising the steps of:
 a. turning an adapter having a first adapter male or female connector having a configuration compatible with the first medical fluid flow connector, the adapter having a second adapter male or female connector having a configuration compatible with the second medical fluid flow connector, a rigid fluid flow conduit positioned between the first and second adapter male or female connectors, and a pair of wings fixedly secured to the fluid flow conduit between the first adapter male or female connector and the second adapter male or female connector, said first adapter connector having a first set of threads and also having a first collar fixedly secured to and radially spaced from the fluid flow conduit and said second adapter connector having a second set of threads and also having a second collar fixedly secured to and radially spaced from the fluid flow conduit with the pair of wings between and spaced from both of the first and second collars;
 b. releasably connecting the first medical fluid flow component connector to the first adapter male or female connector using the first set of threads;
 c. releasably connecting the second medical fluid flow component connector to the second adapter male or female connector using the second set of threads; and
 d. directing a stream of liquid through, and in fluid communication with, a fluid flow lumen of the fluid flow conduit as liquid flows from the first medical fluid flow component to the second medical fluid flow component.

12. A medical fluid flow system comprising:
 a. first and second medical fluid flow components in which the first medical fluid flow component includes a first male Luer or female Luer connector of a first configuration, and the second medical fluid flow component includes a second male Luer or female Luer connector of a second configuration that is not compatible with the first configuration;
 b. an adapter making a fluid connection between first and second medical fluid flow components including:
  i) a rigid fluid flow conduit including a first end and a second end and a fluid flow lumen extending between the first and second ends, said fluid flow conduit including a pair of wings fixedly secured to the fluid flow conduit and adapted to be engaged by a user's fingers when turning the adapter and wherein said fluid flow lumen is configured so that a stream of liquid flows through, and is in fluid communication with, the fluid flow lumen when liquid flows from the first medical fluid flow component to the second medical fluid flow component;
  ii) a first adapter connector positioned at the first end of said fluid flow conduit, said first adapter connector being a male Luer or female Luer having a first set of threads and also having a first collar fixedly secured to and radially spaced from the fluid flow conduit and a first configuration configured to be releasably connected with the first medical fluid flow component connector by the first set of threads;
  iii) a second adapter connector positioned at the second end of said fluid flow conduit so as to be spaced from the first adapter connector by the fluid flow lumen, said second adapter connector being a male Luer or female Luer having a second set of threads and also having a second collar fixedly secured to and radially spaced from the fluid flow conduit and a second configuration configured to be releasably connected with the second medical fluid flow component connector by the second set of threads; and
  iv) said pair of wings fixedly secured to the fluid flow conduit between and spaced from the first adapter connector and the second adapter connector.

13. The adapter of claim 1 wherein each of the pair of wings includes an edge opposing the first collar wherein said edge is tapered away from the first collar in a direction moving radially outwards from said fluid flow conduit.

14. The system of claim 12 wherein each of the pair of wings includes an edge opposing the first collar herein said edge is tapered away from the first collar in a direction moving radially outwards from said fluid flow conduit.

15. The adapter of claim 1 wherein at least the first adapter connector or the second adapter connector complies with Organization for Standardization International Standard ISO 594.

16. The adapter of claim 1 wherein at least the first adapter connector or the second adapter connector complies with Organization for Standardization International Standard ISO 18250.

17. The adapter of claim 1 wherein the first adapter connector complies with Organization for Standardization International Standard ISO 594 and the second adapter connector complies with Organization for Standardization International Standard ISO 18250.

* * * * *